United States Patent [19]

Matsumura

[11] 4,132,466
[45] Jan. 2, 1979

[54] OPHTHALMOSCOPIC OPTICAL SYSTEM

[75] Inventor: Isao Matsumura, Yokohama, Japan

[73] Assignee: Canon Kabushiki Kaisha, Tokyo, Japan

[21] Appl. No.: 729,976

[22] Filed: Oct. 6, 1976

[30] Foreign Application Priority Data

Oct. 9, 1975 [JP] Japan .................. 50-122330

[51] Int. Cl.$^2$ .......................... A61B 3/14; A61B 3/10
[52] U.S. Cl. ................................ 351/7; 351/14; 351/16
[58] Field of Search .................. 351/7, 14, 16; 354/62

[56] References Cited

U.S. PATENT DOCUMENTS

| 3,594,071 | 7/1971 | Okajima | 351/7 |
| 3,851,954 | 12/1974 | Kato | 351/7 |
| 3,925,793 | 12/1975 | Matsumura | 351/7 X |

FOREIGN PATENT DOCUMENTS 1115136 4/1956 France ................................. 351/7

Primary Examiner—Paul A. Sacher
Assistant Examiner—Rodney B. Bovernick
Attorney, Agent, or Firm—Toren, McGeady and Stanger

[57] ABSTRACT

An opthalmoscopic optical system for photographing the fundus of an eye by an ophthalmoscopic camera, it is necessary to illuminate the ocular fundus through the cornea. On the cornea, however, a part of the illuminating light is reflected with the result of production of halo in an image of the ocular fundus. This can be avoided by separating an illuminating light incident area of the cornea from that serving for the emergence of image forming rays to keep this part free from reflexes. According to the present invention, there is positioned between an objective lens and an image-forming lens aligned on a common optical axis is an inclined illuminating plate is positioned between objective lens and an image-forming lens of such construction that a mirrored central area in the vicinity of the optical axis is surrounded by an annular transparent zone which directs light from an illuminating arrangement to the objective lens to suppress the production of a halo.

When the ophthalmoscopic camera is set up at an effective distance from an eye to be examined, as the mirror and the cornea of the eye are conjugate to each other with respect to the objective lens, the illuminating light passes the cornea at a central portion thereof, from an outer annular zone of which emerges light reflected from the ocular fundus.

8 Claims, 5 Drawing Figures

OPHTHALMOSCOPIC OPTICAL SYSTEM

BACKGROUND OF THE INVENTION

This invention relates to optical systems of ophthalmoscopic cameras for observation and photography of the fundus of an eye, and more particularly to a novel optical construction for separating a bundle of illuminating light rays from image-forming rays prior to entering a photographic relay lens, while shielding reflections occurring on the front and rear surfaces of an objective lens adapted to illuminate the fundus of the eye.

The conventional ophthalmoscopic cameras, as, for example, disclosed in British Pat. No. 799,812, generally employ a ring-shaped bundle of illuminating light rays projected onto the cornea of an eye to be examined, so that the rays reflected from the ocular fundus and emerging from the central portion of the cornea produce an image of the ocular fundus at the film plane after having passed through a central hole of an illuminating mirror positioned between an objective lens and a photographic relay lens. This apertured mirror is designed to be suitable for assisting in formation of an image of a ring-shaped slit of the illuminating arrangement without introducing into the image-forming rays disturbing undesirable light due to the reflections on the cornea.

Another source of disturbing reflections of illuminating rays is the surfaces of the objective lens. In order to eliminate such a disadvantage, one solution has been proposed in U.S. Pat. No. 3,594,071. According to this proposal, that portion of the illuminating light which would be subject to reflection from the objective lens surfaces is previously shielded by a small black dot provided on the optical axis in the illuminating optical system.

SUMMARY OF THE INVENTION

An object of the present invention is to increase the outer diameter of a bundle of image-bearing rays incident upon a photographic lens group without causing reduction in image quality due to diffraction which results in a decrease in the resolving power of the lens group.

Another object of the invention is to achieve substantial elimination of the image forming rays from reflexes which are encountered when the illuminating light rays impinge upon surfaces such as those of the cornea and the objective lens prior to reaching the fundus of an eye.

For accomplishing these objects, a solid bundle of illuminating light rays as projected by an objective lens from a secondary image of a light source focused on an illuminating mirror on an optical axis of the objective lens, is employed to illuminate a central portion of the cornea while the image forming rays emerging from the ocular fundus are permitted to project a bundle passing through an annular unilluminated zone of the cornea around the illuminated central area thereof in a given to a photographic relay lens. Further, there is provided a small black dot as positioned of the bundle of image forming light rays at a point behind the illuminating mirror to eliminate the reflexes produced by the incidence of the illuminating light on the surfaces of the objective lens.

Accordingly, the present invention is to provide an optical system for an ophthalmoscopic camera including an objective lens facing an eye to be examined, a rearwardly situated photographic relay lens, and an inclined mirror positioned between said objective lens and said photographic relay lens to reflect a bundle of illuminating light rays from an illuminating optical system to the objective lens. The mirror is so constructed that a central portion is reflective, and an annular zone surrounding the reflective central portion is transparent, and so arranged that only those of the image forming light rays from the ocular fundus which pass through the annular unilluminated zone on the cornea are permitted to enter the photographic relay lens. A central obscuring diaphragm is provided with its black circular disc positioned in coincidence with the optical axis in the path of the image forming light rays behind said mirror to shield that portion of the illuminating light rays from said mirror which is reflected from the objective lens surfaces.

DESCRIPTION OF THE PREFERRED EMBODIMENTS

Figure 1:
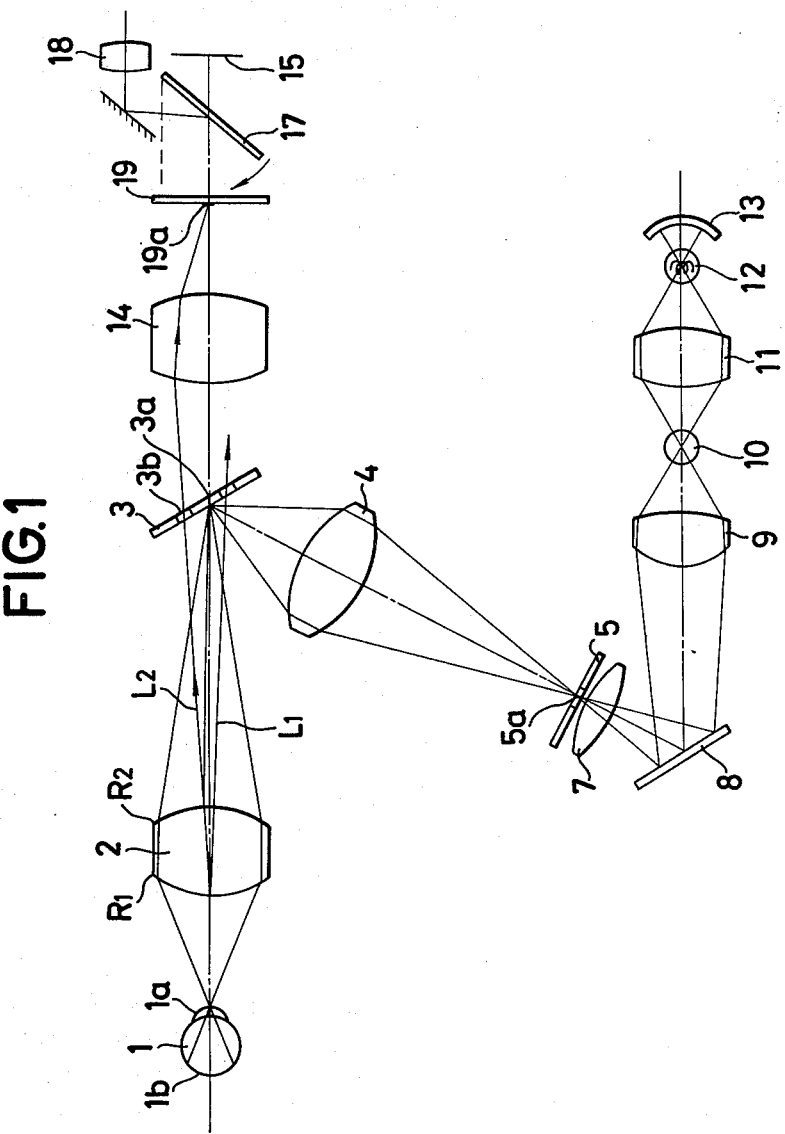
FIG. 1 is a vertical sectional view, partly in block form, of one embodiment of an optical system for an ophthalmoscopic camera according to the present invention.
Figure 3:
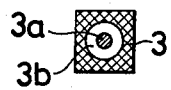
FIG. 3 is a plan view of member 3 shown in FIG. 1.
Figure 4:
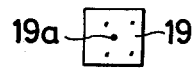
FIG. 4 is a plan view of member 19 shown in FIG. 1.

FIG. 1 shows one embodiment of an ophthalmoscopic system for the observation and photography of the fundus 1b of an eye 1 to be examined according to the invention comprising an objective lens 2 with a front refracting surface $R_1$ (nearest to the eye 1) and a rear refracting surface $R_2$ (farthest from the eye 1) adapted to project a bundle of illuminating light rays to a central portion of the cornea 1a from a secondary image of a light source focused on a central mirrored portion 3a of a reflecting plate 3 by a relay lens 4 constituting part of an illuminating system. As shown in FIG. 3, the central mirrored portion 3a of the plate 3 has a small diameter compared with an effective aperture of the system and is surrounded by an annular transparent zone 3b. The reflecting plate 3 is inclined with respect to an optical axis of the objective lens 2, and is located with the center of the central mirrored portion 3a coinciding with the optical axis.

Figure 2:
FIG. 2 is a plan view of member 5 shown in FIG. 1.

The illuminating system further includes an apertured diaphragm 5 of which the construction is shown in FIG. 2 and located at a conjugate point to the mirror 3 with respect to the relay lens 4, a field lens 7, a planar mirror 8, first and second condenser lenses 9 and 11, first and second light sources 10 and 12 such as a stroboscopic lamp for 10 and a tungusten lamp for 12, and a concave mirror 13, these parts 4, 5, 7, 9, 10, 11, 12 and 13 being arranged on a common optical axis which intersects the optical axis of the objective lens 2 at a point on which the center of the mirrored portion 3a is situated. An image of the tungusten filament coil 12 is first formed by the second condenser lens 11 at a center of the stroboscopic lamp 10 and then refocused by the first condenser lens 9 at or near the aperture 5a of the diaphragm 5 after reflection from the mirror 8 and passing through the field lens 7. Also formed on the aperture diaphragm 5 is an image of the stroboscopic lamp 10.

Located behind the illuminating mirror 3 is a photographic relay lens 14 with its optical axis coinciding with the optical axis of the objective lens 2 to form a real image of the fundus 1b of the eye 1 at a focal plane 15 which image can be observed through an eye-piece 18 with the aid of a tiltable mirror 17 as illustrated.

With the ophthalmoscopic camera of FIG. 1 set up at an effective distance where the cornea or pupil 1a of the eye 1 and the illuminating mirror 3a are conjugate to each other with respect to the objective lens 2, upon energization of either of the first and second light sources 10 and 12, a first image of the light source is formed at the aperture 5a of the apertured diaphragm 5 and then transferred by the relay lens to a second image focused on or near the central mirrored portion 3a of the reflecting mirror 3 serving as a secondary light source for providing a bundle of illuminating light rays which is focused on a central portion of the cornea or pupil 1a of the eye 1 by the objective lens 2. A bundle of light rays emerging from the illuminated fundus 1b of the eye 1 after converging at a point between the objective lens 2 and the illuminating mirror 3a impinges on the mirror 3 over the entire effective area thereof somewhat larger than the annular transparent zone 3b. This transparent zone 3b is so dimensioned that those of the image-forming rays which emerge from the annular unilluminated area on the cornea 1a are permitted to pass through the zone 3b to the photographic relay lens 14 by which an image of the ocular funds 1b is formed on a light-sensitive material at the focal plane 15 when the tiltable mirror 17 is in its non-viewing position. Thus, the cross-sectional area of a bundle of image-forming light rays can be increased in this way with increase in the resolving power.

Figure 5:
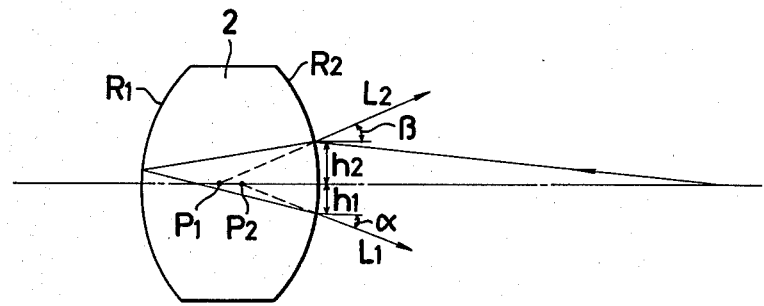
FIG. 5 is a diagram of geometry considered in determining an objective lens 2 of FIG. 1 to permit a single central obscuring diaphragm 19 to shield reflections of the illuminating light rays from the front and rear surfaces of objective lens 2.

On the other hand, when the illuminating beam of light rays passes through the objective lens, portions of the beam of light are reflected at both the front and rear surfaces of the objective lens. Such reflexes caused by both surfaces of the objective lens are undesirable and are eliminated in a manner as illustrated in FIGS. 1 and 5. FIG. 5 illustrates the details of the objective lens shown in FIG. 1. Referring to FIG. 1, an image of the aperture 5a illuminated by the light source is formed through the relay lens 4 on the central mirror portion 3a of the reflecting mirror 3. Of beams of illumination light reflected by the mirrored portion 3a, a light portion L2 which has been reflected by the rear surface R2 of the objective lens 2 and a light portion L1 which has been reflected by the front surface R1 of the objective lens pass through the transparent zone 3b and are converged by the photographic relay lens 14 on the optical axis respectively. With a black dot or disc 19a arranged in a position at which the above stated reflexes converge, the reflexes which are undesirable can be blocked by the black disc and thus can be prevented from reaching the light sensitive focal plane 15. Then, in cases where the reflex L1 converges at a point different from a point at which the reflex L2 converges, either two black dis-shaped dots are arranged at such different points or a large sized black disc-shaped dot is arranged to block such reflexes. However, if the size of such a black dot is excessively large, it would also block the image forming rays. The use of a large sized block dot is, therefore, not preferable. The following description covers a method for making the converging points of reflexes L1 and L2 coincide with each other in conjunction with FIG. 5:

In the bundle of the illuminating fine beams of light, each beam is incident upon the lens surface R2. Some of such fine beams of light then form the reflex L2. Let us assume that the incident height, i.e. a distance between the incident point and the optical axis, is h2 and an angle formed between the beam and the optical axis is $\alpha$; and a point at which a line extended form the beam L2 in the direction reverse to its direction intersects the optical axis is P1. A virtual image of the image of the aperture 5a is formed at the point P1. Meanwhile, some of the fine beams incident upon the objective lens 2 are then reflected by the other surface R1 of the lens to emerge from the lens surface R2. Let us assume that such beams form the reflex beam L1; the emerging height, i.e. a distance between the emerging point and the optical axis is h1; an angle formed between the beam L1 and the optical axis is $\beta$; and a point at which a line extended from the beam L1 in the direction reverse to its direction intersects the optical axis is P2. A virtual image of the image of the aperture 5a is formed at the point P2.

As analytically described in the foregoing, the beam L2 appears as though it emerges from the point P1 while the beam L1 appears as though it emerges from the point P2. Accordingly, if the point P1 and the point P2 are arranged to be superposed upon each other, the beams L1 and L2 would behave as though they emerge from the same point and thus could be converged on the same place by relay lens 14. Then, in order to superpose the points P1 and P2 on each other, the objective lens 2 should be arranged to satisfy a relation of $\alpha/h1 = \beta/h2$, which can be obtained by selecting a suitable radius of curvature for each of the front and rear surfaces of the lens and suitable distance between the lens surfaces.

Since the objective lens shown in FIG. 1 is arranged to satisfy the above stated relation, the reflex beams L1 and L2 image on the black dot 19a and the size of the dot can be very small.

An advantage of the invention is that the resolving power of the system can be improved by increasing the diameter of a bundle of image-forming light rays as it passes through an annular transparent zone of the illuminating mirror over the prior art employing an apertured illuminating mirror.

Another advantage lies in that, since the secondary light source formed on the cornea is located on the optical axis, the influence of spherical aberation is reduced to a minimal degree. This, therefore, ensures that the eye fundus illuminating bundle of light rays are effectively separated from the image forming rays.

Still another advantage is an increase in the relative intensity ratio of the image forming light to the illuminating light with a decrease in the relative amount of flare produced from the reflections of light rays on the inside wall of the lens mounting mechanism and the like because of the extremely small reflectance of the ocular fundus.

What is claimed is:
1. An ophthalmoscopic optical system comprising:
    (a) a front optical member facing an eye with a fundus to be examined and having an optical axis;
    (b) an image forming lens positioned on the image side of said front optical member in axial alignment therewith;
    (c) an illuminating arrangement including at least one light source, a lens group and an apertured member and having an optical axis;

(d) a reflecting member having a reflecting plane surrounded by an annular zone, said reflecting plane coinciding with a point at which the optical axis of said front optical member and that of said illuminating arrangement intersect each other, said reflecting plane being positioned to reflect toward the eye light emitted by said light source and passing through said apertured member; of said illuminating arrangement and (e) said annular zone including a transparent aperture, said transparent aperture being disposed between said front optical member and said image forming lens for passing image-forming rays.

2. An ophthalmoscopic optical system comprising:
(a) a front optical member facing an eye with a fundus to be examined and having an optical axis;
(b) an image forming lens positioned on the image side of said front optical member in axial alignment therewith;
(c) an illuminating arrangement including at least one light source, a lens group and an apertured member and having an optical axis;
(d) a reflecting member having a reflecting plane surrounded by an annular zone, said reflecting plane coinciding with a point at which the optical axis of said front optical member and that of said illuminating arrangement intersect each other, said reflecting plane being positioned to reflect toward the eye light emitted by said light source and passing through said apertured member of said illuminating arrangement; and
(e) said annular zone including a transparent aperture, said transparent aperture being disposed between said front optical member and said image forming lens for passing image-forming rays.
and wherein said reflecting member has a central mirrored portion surrounded by said annular zone.

3. An ophthalmoscopic optical system as claimed in claim 1, further including at least one small light-shielding region on the optical axis at a location between said image forming lens and an image plane.

4. An ophthalmoscopic optical system as claimed in claim 3, wherein said small light-shielding region is a transparent plate with a black disc.

5. An ophthalmoscopic optical system comprising:
(a) a front optical member facing an eye with a fundus to be examined and having an optical axis;
(b) an image forming lens positioned on the image side of said front optical member in axial alignment therewith;
(c) an illuminating arrangement including at least one light source, a lens group and an apertured member and having an optical axis;
(d) a reflecting member having a reflecting plane surrounded by an annular zone, said reflecting plane coinciding with a point at which the optical axis of said front optical member and that of said illuminating arrangement intersect each other, said reflecting plane being positioned to reflect toward the eye light emitted by said light source and passing through said apertured member of said illuminating arrangement; and (e) said annular zone including a transparent aperture, said transparent aperture being disposed between said front optical member and said image forming lens for passing image-forming rays;
wherein said front optical member is an objective lens, said image forming lens is a photographic relay lens situated rearwardly therefrom in axial alignment therewith, said reflecting member is a reflecting plate having a central mirrored portion and said annular zone being disposed around said central mirrored portion and disposed between said objective lens and said photographic relay lens inclined at an angle to the optical axis, and said illuminating arrangement including light sources for illumination and photography of which images are formed at a common conjugate point to said central mirrored portion of said reflection plate with respect to a relay lens.

6. An ophthalmoscopic optical system as claimed in claim 5, wherein the image of said light source is formed on said apertured member by a condensor lens.

7. An ophthalmoscopic optical system as claimed in claim 5, further including at least one transparent plate positioned behind said photographic relay lens and provided with a black dot located at a point at which said transparent plate intersects the optical axis.

8. An ophthalmoscopic optical systemas claimed in claim 5, wherein said objective lens is of bi-convex configuration having front and rear-curved surfaces having radii of curvature for which:

$$\alpha/h_1 = \beta/h_2$$

wherein $\alpha$ is the angle of emergence with respect to the optical axis of an illuminating ray after entering said objective lens through the rear surface ($R_2$) thereof followed by reflection from the front surface ($R_1$) thereof to the rear surface ($R_2$);
$h_1$ is the height of emergence;
$\beta$ is the angle of incidence with respect to the optical axis of an illuminating ray impinging on the rear surface ($R_2$) of said objective lens from the image side followed by reflection therefrom; and
$h_2$ is the height of incidence.

* * * * *